United States Patent [19]
Ryan

[11] Patent Number: 6,152,923
[45] Date of Patent: Nov. 28, 2000

[54] MULTI-CONTACT FORCEPS AND METHOD OF SEALING, COAGULATING, CAUTERIZING AND/OR CUTTING VESSELS AND TISSUE

[75] Inventor: Thomas Ryan, Fort Collins, Colo.

[73] Assignee: Sherwood Services AG, Schaffhausen, Switzerland

[21] Appl. No.: 09/301,270

[22] Filed: Apr. 28, 1999

[51] Int. Cl.[7] ................................................. A61B 18/18
[52] U.S. Cl. ............................. 606/51; 606/42; 606/48
[58] Field of Search ........................... 606/41, 45, 48–52, 606/42

[56] References Cited

U.S. PATENT DOCUMENTS

| | | |
|---|---|---|
| 371,664 | 10/1887 | Brannan et al. . |
| 702,472 | 6/1902 | Pignolet . |
| 728,883 | 5/1903 | Downes . |
| 1,586,645 | 6/1926 | Bierman . |
| 2,002,594 | 5/1935 | Wappler et al. . |
| 2,176,479 | 10/1939 | Willis . |
| 2,518,994 | 8/1950 | Miller . |
| 3,404,677 | 10/1968 | Springer . |
| 3,515,139 | 6/1970 | Malina . |
| 3,643,663 | 2/1972 | Sutter . |
| 3,651,811 | 3/1972 | Hildebrandt et al. . |
| 3,895,636 | 7/1975 | Schmidt . |
| 3,920,021 | 11/1975 | Hiltebrandt . |
| 3,938,527 | 2/1976 | Rioux et al. . |
| 3,952,749 | 4/1976 | Fridolph et al. . |
| 4,005,714 | 2/1977 | Hiltebrandt . |
| 4,370,980 | 2/1983 | Lottick . |
| 4,552,143 | 11/1985 | Lottick . |
| 4,597,379 | 7/1986 | Xihn et al. . |
| 4,671,274 | 6/1987 | Sorochenko . |
| 4,685,459 | 8/1987 | Xoch et al. . |
| 4,763,669 | 8/1988 | Jaeger . |
| 4,836,205 | 6/1989 | Barrett . |
| 4,887,612 | 12/1989 | Esser et al. . |
| 4,938,761 | 7/1990 | Ensslin . |
| 4,985,030 | 1/1991 | Melzer et al. ....................... 606/51 |
| 5,026,370 | 6/1991 | Lottick . |
| 5,116,332 | 5/1992 | Lottick . |
| 5,147,356 | 9/1992 | Bhatta . |

(List continued on next page.)

FOREIGN PATENT DOCUMENTS

| | | |
|---|---|---|
| 2104423 | 2/1994 | Canada . |
| 0 584 787 A1 | 3/1994 | European Pat. Off. . |
| 0 853 922 A1 | 7/1998 | European Pat. Off. . |
| 401367 | 11/1974 | U.S.S.R. . |

OTHER PUBLICATIONS

Sigel et al., "The Mechanism of Blood Vessel Closure by High Frequency Electrocoagulation." Surgery Gynecology & Obstetrics, Oct. 1965 pp. 823–831.

Bergdahl et al. "Studies on Coagulation and the Development of an Automatic Computerized Bipolar Coagulator", J. Neurosurg, vol. 75, Jul. 1991, pp. 148–151.

International Search Report—PCT/US98/18640.
International Search Report—PCT/US98/23950.

*Primary Examiner*—Linda C. M. Dvorak
*Assistant Examiner*—Roy Gibson

[57] ABSTRACT

A bipolar forceps for sealing, cauterizing, coagulating and/or cutting vessels and vascular tissue at multiple sites includes a pair of multi-pronged jaw members pivotally attached in opposing relation relative to one another and selectively movable from an open position wherein the jaw members are disposed in spaced relation relative to one another to a second clamping position wherein the jaw members cooperate to grasp tissue therebetween. The forceps also includes at least one electrode disposed on the inner facing surface of each prong of the jaw members and a switch for selectively controlling electrosurgical energy to each electrode. The electrodes on each of the jaw members can be activated simultaneously, sequentially, or in a multiplexed fashion. The disclosure also relates to a method of sealing, cauterizing, coagulating and/or cutting vessels and vascular tissue at multiple sites without manipulation of the forceps.

18 Claims, 5 Drawing Sheets

U.S. PATENT DOCUMENTS

| | | |
|---|---|---|
| 5,151,102 | 9/1992 | Xamiyama et al. . |
| 5,197,493 | 3/1993 | Grier-Idris . |
| 5,199,441 | 4/1993 | Hogle . |
| 5,217,458 | 6/1993 | Parins . |
| 5,217,460 | 6/1993 | Knoepfler . |
| 5,250,047 | 10/1993 | Rydell . |
| 5,258,006 | 11/1993 | Rydell et al. . |
| 5,263,967 | 11/1993 | Lyons, III et al. . |
| 5,277,201 | 1/1994 | Stern . |
| 5,282,800 | 2/1994 | Foshee et al. . |
| 5,282,826 | 2/1994 | Quadri . |
| 5,324,289 | 6/1994 | Eggers . |
| 5,330,471 | 7/1994 | Eggers . |
| 5,336,221 | 8/1994 | Anderson . |
| 5,342,359 | 8/1994 | Rydell . |
| 5,342,389 | 8/1994 | Haber et al. . |
| 5,352,222 | 10/1994 | Rydell . |
| 5,356,408 | 10/1994 | Rydell . |
| 5,372,589 | 12/1994 | Davis . |
| 5,389,104 | 2/1995 | Hahnen et al. . |
| 5,391,166 | 2/1995 | Eggers . |
| 5,403,312 | 4/1995 | Yates et al. . |
| 5,431,674 | 7/1995 | Basile et al. . |
| 5,443,463 | 8/1995 | Stern et al. . |
| 5,443,464 | 8/1995 | Russell et al. . |
| 5,443,479 | 8/1995 | Bressi, Jr. . |
| 5,445,658 | 8/1995 | Durrfeld et al. . |
| 5,456,684 | 10/1995 | Schmidt et al. . |
| 5,458,598 | 10/1995 | Feinberg et al. . |
| 5,462,546 | 10/1995 | Rydell . |
| 5,472,443 | 12/1995 | Cordis et al. . |
| 5,478,351 | 12/1995 | Meade et al. . |
| 5,484,436 | 1/1996 | Eggers et al. . |
| 5,486,172 | 1/1996 | Chess . |
| 5,507,772 | 4/1996 | Shutt et al. . |
| 5,509,922 | 4/1996 | Aranyi et al. . |
| 5,527,313 | 6/1996 | Scott et al. . |
| 5,531,744 | 7/1996 | Nardella et al. . |
| 5,540,684 | 7/1996 | Hassler, Jr. . |
| 5,549,623 | 8/1996 | Sharpe et al. . |
| 5,558,672 | 9/1996 | Edwards et al. . |
| 5,562,720 | 10/1996 | Stern et al. . |
| 5,569,241 | 10/1996 | Edwardds . |
| 5,573,535 | 11/1996 | Viklund . |
| 5,615,690 | 4/1997 | Giurtino et al. . |
| 5,626,578 | 5/1997 | Tihon . |
| 5,637,110 | 6/1997 | Pennybacker et al. . |
| 5,658,281 | 8/1997 | Heard . |
| 5,667,526 | 9/1997 | Levin . |
| 5,674,220 | 10/1997 | Fox et al. . |
| 5,683,388 | 11/1997 | Slater . |
| 5,693,051 | 12/1997 | Schulze et al. . |
| 5,700,261 | 12/1997 | Brinkerhoff . |
| 5,700,276 | 12/1997 | Benecke . |
| 5,702,390 | 12/1997 | Austin et al. . |
| 5,709,707 | 1/1998 | Lock et al. . |
| 5,713,896 | 2/1998 | Nardella ............................ 606/50 |
| 5,720,744 | 2/1998 | Eggleston et al. . |
| 5,728,160 | 3/1998 | Draenert . |
| 5,730,752 | 3/1998 | Alden et al. . |
| 5,735,848 | 4/1998 | Yates et al. . |
| 5,755,717 | 5/1998 | Yates et al. . |
| 5,766,166 | 6/1998 | Hooven . |
| 5,769,849 | 6/1998 | Eggers . |
| 5,776,128 | 7/1998 | Eggers . |
| 5,776,130 | 7/1998 | Buysse et al. . |
| 5,810,802 | 9/1998 | Panescu et al. . |
| 5,817,091 | 10/1998 | Nardella et al. . |
| 5,817,093 | 10/1998 | Williamson, IV et al. . |
| 5,827,281 | 10/1998 | Levin . |
| 5,833,690 | 11/1998 | Yates et al. . |
| 5,891,142 | 4/1999 | Eggers et al. ...................... 606/51 |
| 5,951,549 | 9/1999 | Richardson et al. .- |

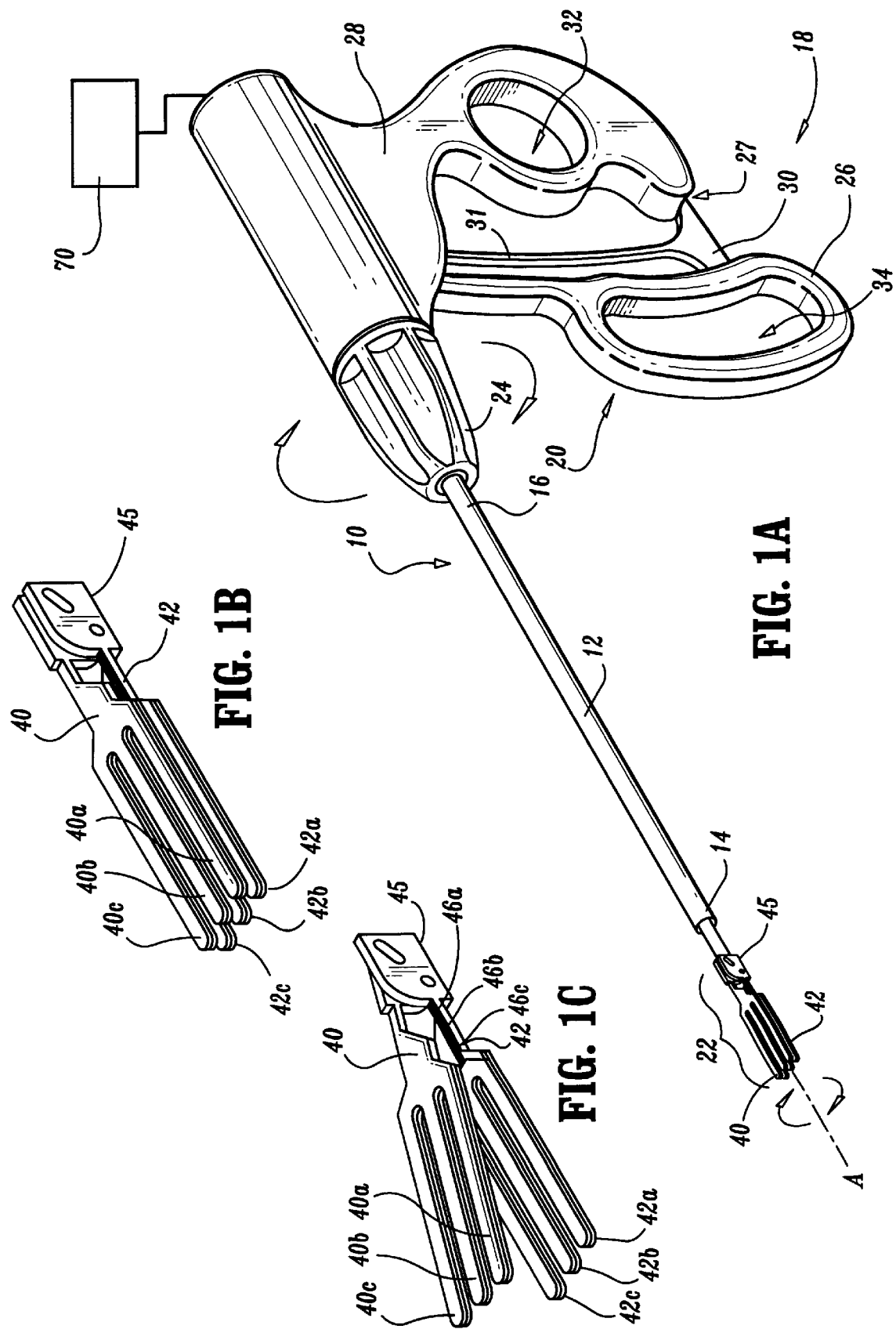

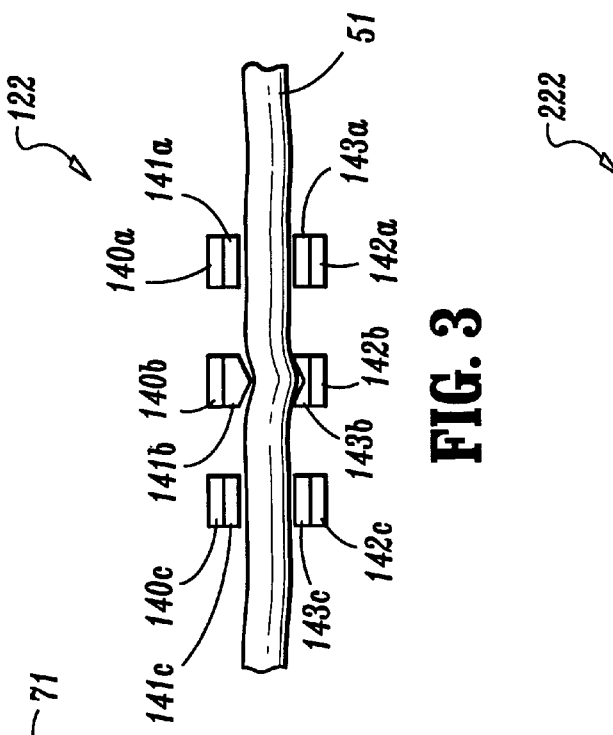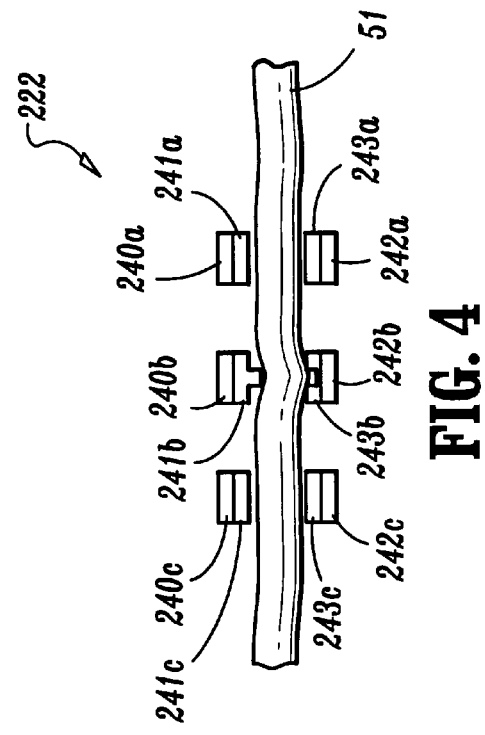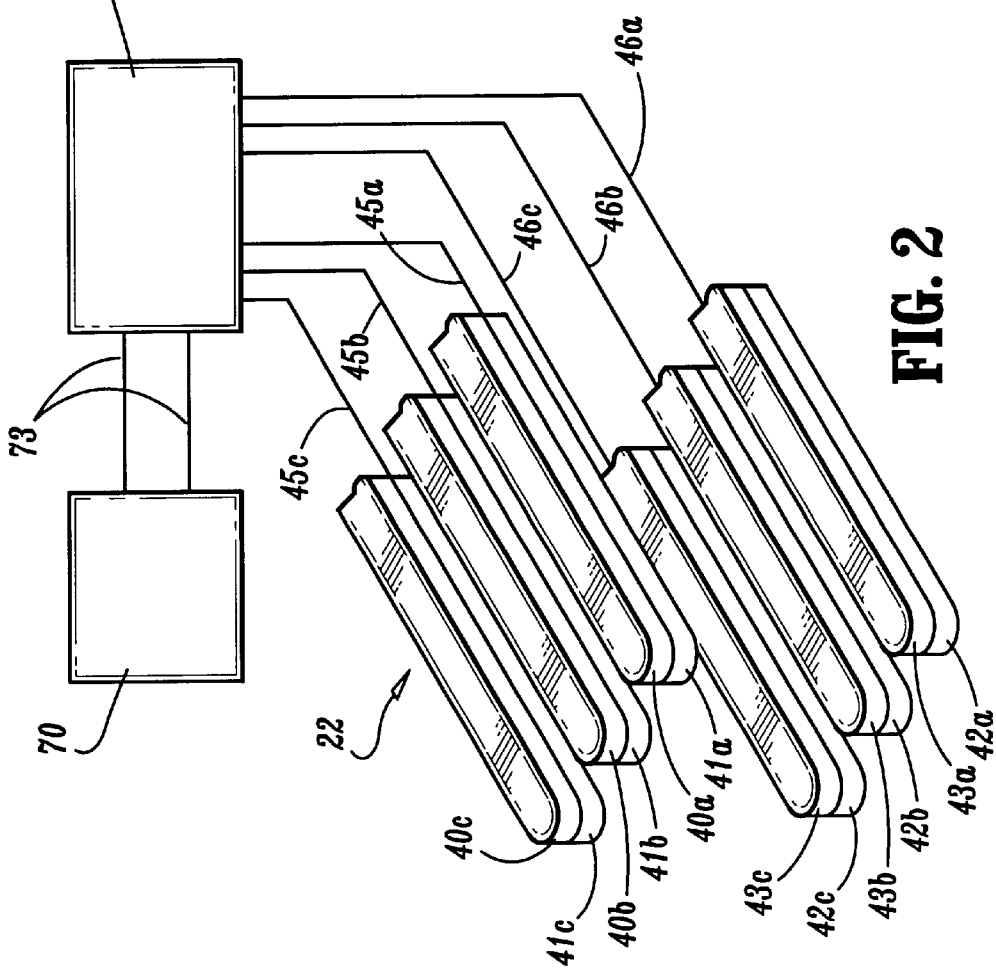

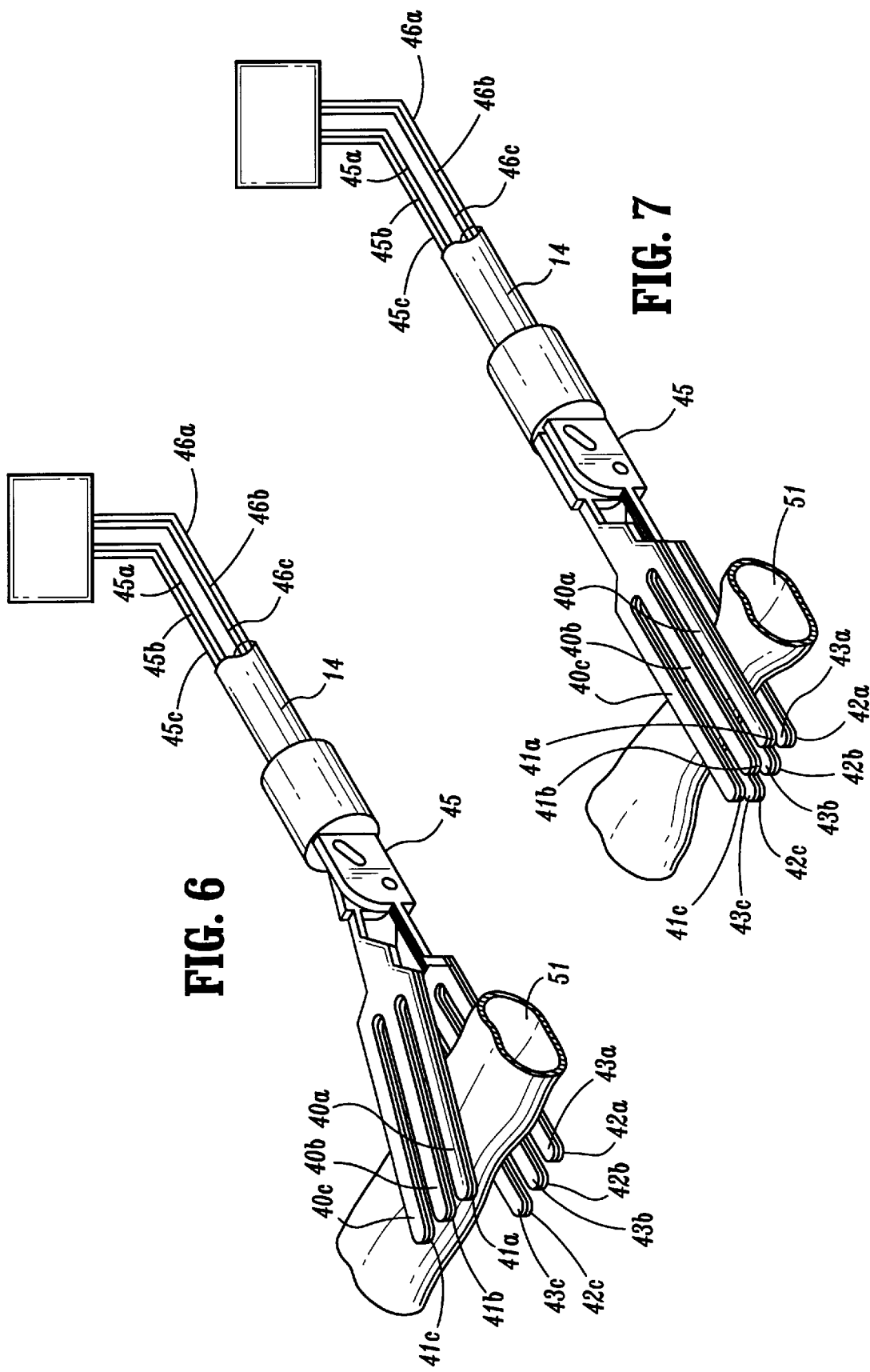

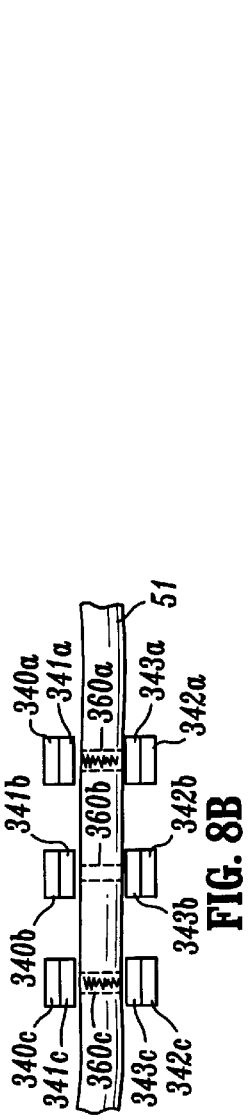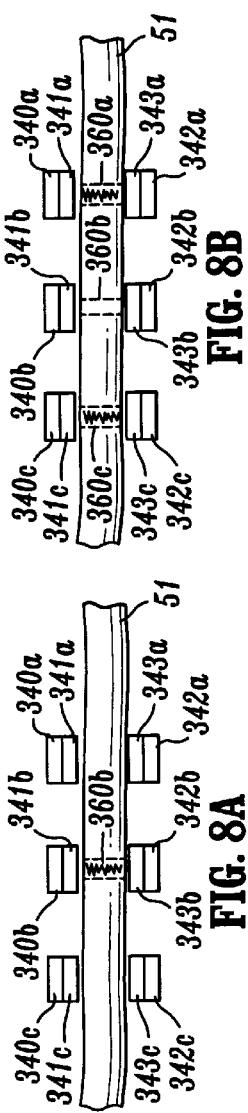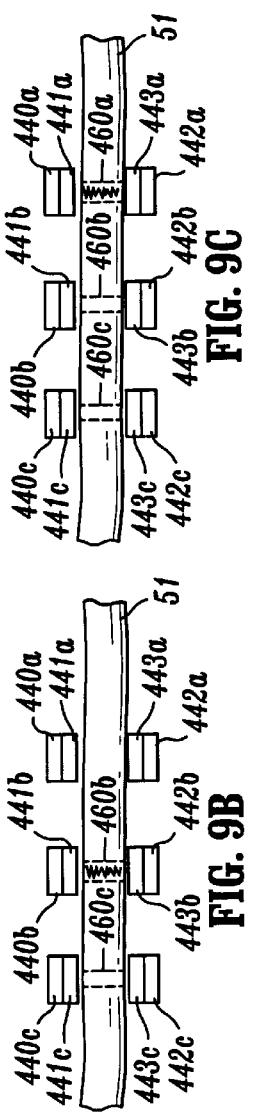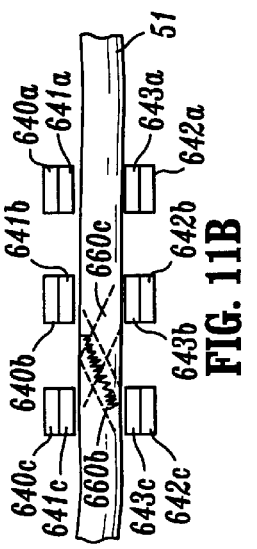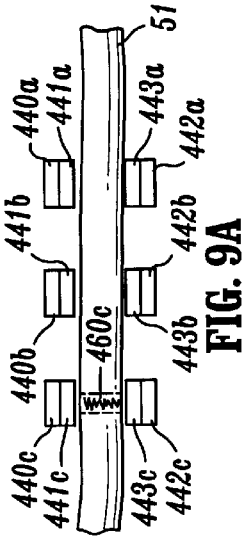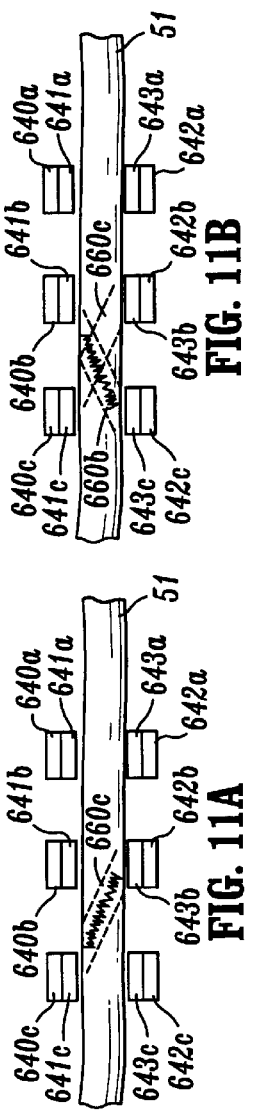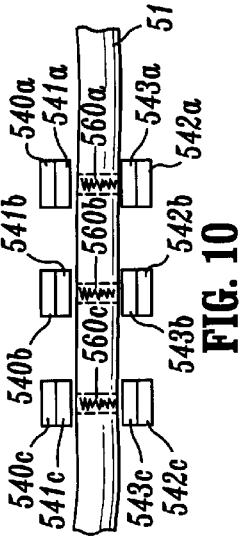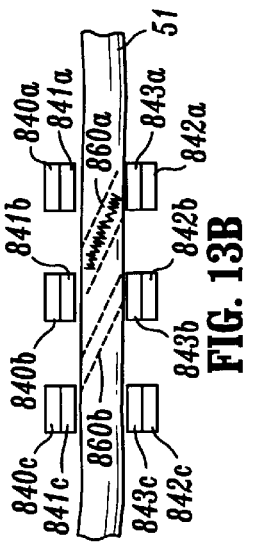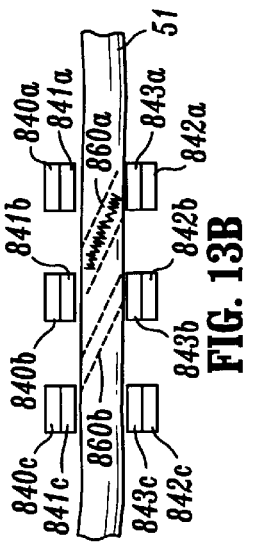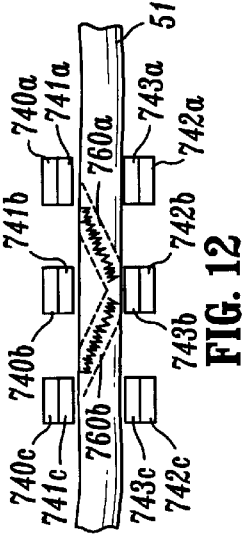

MULTI-CONTACT FORCEPS AND METHOD OF SEALING, COAGULATING, CAUTERIZING AND/OR CUTTING VESSELS AND TISSUE

BACKGROUND

The present disclosure relates to hemostats or forceps used for open surgical procedures and laparoscopic surgical procedures. More particularly, the present disclosure relates to a multi-pronged bipolar forceps which allows a user to selectively seal, cauterize, coagulate/desiccate and/or cut vessels and vascular tissue at multiple sites without manipulating the forceps.

1. Technical Field

A hemostat or forceps is a simple plier-like tool which uses mechanical action between its jaws to constrict tissue and is commonly used in surgical procedures to grasp, dissect and/or clamp tissue. Electrosurgical forceps utilize both mechanical clamping action and electrical energy to effect hemostasis by heating the tissue and blood vessels to coagulate, cauterize, cut and/or seal tissue.

By controlling the intensity, frequency and duration of the electrosurgical energy applied to the tissue, a surgeon can either cauterize, coagulate/desiccate and/or cut tissue and/or simply reduce or slow bleeding. Generally, the electrical configuration of electrosurgical forceps can be categorized in two classifications: 1) monopolar electrosurgical forceps; and 2) bipolar electrosurgical forceps.

Monopolar forceps utilize one active electrode associated with the clamping end effector and a remote patient return electrode or pad which is attached externally to the patient. When electrosurgical energy is applied, the energy travels from the active electrode, to the surgical site, through the patient and to the return electrode.

Bipolar electrosurgical forceps utilize two generally opposing electrodes which are disposed on the inner opposing surfaces of the end effectors and which are both electrically coupled to an electrosurgical generator. Each electrode is charged to a different electric potential. Since tissue is a conductor of electrical energy, when the effectors are utilized to clamp or grasp tissue therebetween, the electrical energy can be selectively transferred through the tissue.

The process of coagulating small vessels is fundamentally different from vessel sealing. For the purposes herein the term coagulation is defined as a process of desiccating tissue wherein the tissue cells are ruptured and dried. Vessel sealing is defined as the process of liquefying the collagen in the tissue so that it cross-links and reforms into a fused mass. Thus, coagulation of small vessels is sufficient to close them, however, larger vessels need to be sealed to assure permanent closure.

In order to effect a proper seal with larger vessels, two predominant mechanical parameters must be accurately controlled—the pressure applied to the vessel and the gap between the electrodes both of which affect thickness of the sealed vessel. More particularly, accurate application of the pressure is important to oppose the walls of the vessel, to reduce the tissue impedance to a low enough value that allows enough electrosurgical energy through the tissue, to overcome the forces of expansion during tissue heating and to contribute to the end tissue thickness which is an indication of a good seal. In some instances a fused vessel wall is optimum between 0.015 and 0.060 millimeters (0.006 to 0.020 inches).

As mentioned above, electrosurgical energy may be applied through the tissue to halt or prevent bleeding. Traditionally, forceps are used to create a single seal per application of electrosurgical energy. Additional seals are made by moving/manipulating the forceps to a second sealing site and applying more electrosurgical energy. For example, when vessels need to be sealed and cut, a surgeon typically makes two seals and cuts between the seals or the surgeon makes three seals and cuts along the centerline of the middle seal. To make these two or three seals, the surgeon manipulates the forceps two or three times and applies electrosurgical energy after each manipulation. This process can be time consuming especially when cutting multiple vessels.

Numerous bipolar electrosurgical forceps have been proposed in the past for various surgical procedures. However, none of these forceps are designed to seal vessels at multiple sealing sites without manipulating the forceps. For example: U.S. Pat. Nos. 2,176,479 to Willis; 4,005,714 to Hiltebrandt; 4,370,980, 4,552,143, 5,026,370 and 5,116,332 to Lottick; 5,443,463 to Stern et al.; 5,702,390 to Austin et al.; and 5,484,436 to Eggers et al., all relate to electrosurgical instruments for coagulating, cutting and/or sealing vessels or tissue.

Stern et al. relates to a coagulating device which utilizes a series of electrodes disposed on an inner facing surface of one end effector with a corresponding pair of temperature sensors disposed on the opposite end effector for sensing the temperature rise in the tissue and providing feedback to an electrosurgical generator to control the rate of coagulation of the tissue.

Austin relates to a bipolar instrument which utilizes a triangularly-shaped electrode pivotally disposed between two parallel electrodes. The triangularly-shaped electrode can be positioned such that in the closed configuration the base of the triangle coagulates tissue between the two parallel electrodes or the triangularly-shaped electrode can be positioned such that in the closed configuration the triangle apex cuts tissue between the two parallel electrodes.

Thus, there exists a need to develop a bipolar forceps which can effectively seal, cauterize, coagulate and/or cut vessels and tissue at multiple tissue sites without manipulating the forceps.

SUMMARY

The present disclosure relates to a bipolar forceps which includes a pair of multi-pronged jaw members pivotally attached in opposing relation relative to one another which are selectively movable from a first open position wherein the jaw members are disposed in spaced relation relative to one another to a second clamping position wherein the jaw members cooperate to grasp and apply pressure to tissue therebetween. At least one electrode is disposed on the inner facing surface of each prong of the jaw members. A switch selectively controls electrosurgical energy to each electrode.

Preferably, the jaw members are bifurcated and each prong/tine of the first jaw member aligns with a corresponding prong of the second jaw member. Jaw members having three, four, five, etc. prongs are also contemplated.

In one embodiment, the inner facing surface of at least one electrode has a shaped or formed cross-section, e.g., V-shaped, corrugated and/or notched, so as to enhance sealing, coagulating, and/or cutting the tissue.

Other embodiments of the present disclosure relate to a method of applying electrosurgical energy to tissue to effectively seal, coagulate, cauterize and/or cut tissue. The method includes the steps of: 1) providing a bipolar forceps as described above; 2) grasping tissue between the jaw members; 3) selectively activating a first electrode on a first of the prongs of the first jaw member; and selectively activating a second electrode on a first of the prongs of the second jaw member. Other methods of the present disclosure include selectively activating additional electrodes on additional prongs of the first and second jaw members to create multiple seals without manipulating the forceps.

Preferably, the electrodes can be activated simultaneously, sequentially and/or multiplexed depending upon a particular purpose and/or to promulgate a particular electrosurgical result.

Another method according the present disclosure relates to a method of sealing vessels which includes the steps of: 1) providing a bipolar forceps having: a pair of multi-pronged jaw members pivotally attached in opposing relation relative to one another and movable from a first open position to a second clamping position to grasp tissue therebetween, at least one pair of opposing electrodes disposed on each opposing pair of prongs of the jaw members, and a switch for selectively controlling electrosurgical energy to each electrode; 2) grasping tissue between the jaw members; and 3) selectively activating each of the pairs of opposing electrodes to form a seal between each pair of opposing electrodes.

BRIEF DESCRIPTION OF THE DRAWINGS

FIG. 1A is a perspective view of a multi-pronged bipolar forceps according to the present disclosure;

FIG. 1B is an enlarged, perspective view of an end effector of the bipolar forceps shown in the closed configuration;

FIG. 1C is an enlarged, perspective view of the end effector shown in the open configuration;

FIG. 2 is an enlarged, fragmentarily-illustrated perspective view of the individual prongs of a trifurcated end effector shown coupled to a switching mechanism;

FIG. 3 is front view of an alternate embodiment of the end effector wherein the inner facing surfaces of the middle opposing electrodes form a V-shaped mechanical interface;

FIG. 4 is front view of an alternate embodiment of the end effector wherein the inner facing surfaces of the middle opposing electrodes form a notch-like mechanical interface;

FIG. 6 is a perspective view showing the forceps of FIG. 1 in the open configuration prior to engagement about a tubular vessel;

FIG. 7 is a perspective view showing the forceps of FIG. 1 in the closed configuration compressing a tubular vessel;

FIGS. 8A and 8B are front views of the forceps showing one particular electrode pair activation sequence for sealing tissue at multiple sealing sites;

FIGS. 9A–9C are front views of the forceps showing another electrode pair activation sequence for sealing tissue at multiple sealing sites;

FIG. 10 is a front view of the forceps showing simultaneous activation of the electrode pairs;

FIGS. 11A and 11B are front views of the forceps showing another electrode pair activation sequence wherein vertically off-set pairs of electrodes are activated to form an X-shaped cross-seal;

FIG. 12 is a front view of the forceps showing simultaneous activation of one lower electrode forming two cross-seals with two upper, vertically off-set electrodes; and FIGS. 13A and 13B are front views of the forceps showing another electrode activation sequence for cross-sealing tissue at multiple sealing sites.

DETAILED DESCRIPTION OF THE PREFERRED EMBODIMENTS

Figure 5:
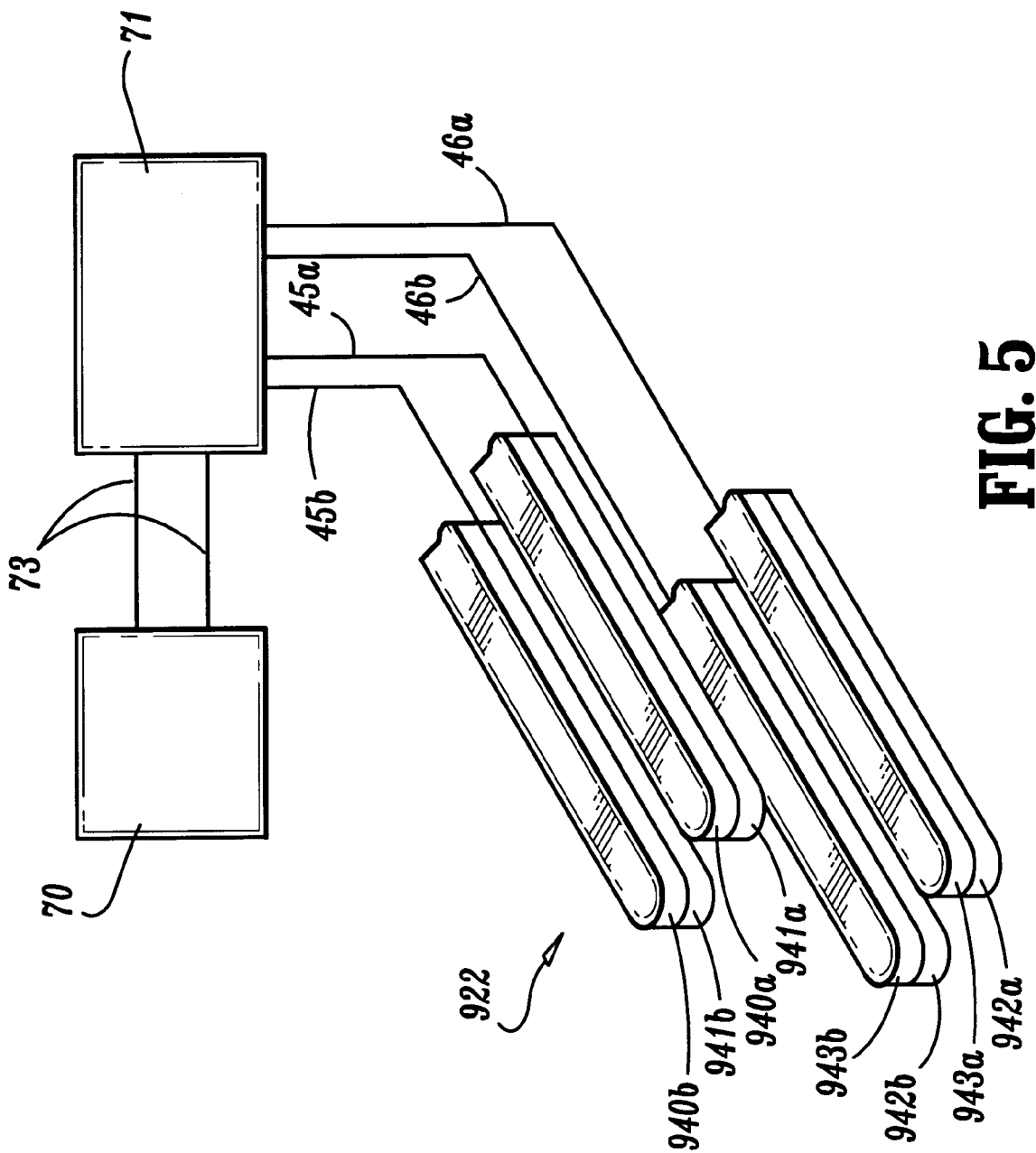
FIG. 5 is an enlarged, fragmentarily-illustrated perspective view of the individual prongs of a bifurcated end effector shown coupled to a switching mechanism.

Referring now to FIG. 1A, a forceps 10 for use with open and/or laparoscopic surgical procedures includes an elongated shaft portion 12 having a proximal end 16 and a distal end 14. In the drawings and in the description which follows, the term "proximal", as is traditional, will refer to the end of the forceps 10 which is closer to the user, while the term "distal" will refer to the end which is further from the user.

An end effector assembly 22 is attached to the distal end 14 of shaft 12 and includes a pair of opposing multi-pronged jaw members 40 and 42. Preferably, end effector assembly 22 is trifurcated and includes a middle or central pair of opposing prongs 40b and 42b and two pair of outer opposing prongs 40a, 42a and 40c, 42c (see FIGS. 1B and 1C). Handle portion 18 is attached to the proximal end 16 of shaft 12 and includes an activator assembly 20 for imparting movement of the jaw members 40 and 42 from an open position wherein the jaw members 40, 42 are disposed in spaced relation relative to one another, to a clamping or closed position wherein the jaw members 40, 42 cooperate to compress tissue 51 therebetween (see FIGS. 6 and 7).

Activator assembly 20 includes a movable handle 26 having an aperture 34 defined therein for receiving at least one of the operator's fingers and a fixed handle 28 having an aperture 32 defined therein for receiving an operator's thumb. Movable handle 26 is selectively moveable from a first position relative to fixed handle 28 to a second position in closer proximity to the fixed handle 28 to approximate jaw members 40, 42. Preferably, fixed handle 28 includes a channel 27 which extends proximally for receiving a ratchet 30 which is coupled to movable handle 26. This structure allows for progressive closure of end effector assembly 22 as well as locking the juxtaposed position of opposing jaw members 40, 42.

In some cases it may be preferable to include other mechanisms to control and/or limit the movement of handle 26 relative to handle 28 such as, e.g., hydraulic, semi-hydraulic and/or gearing systems.

Handle portion 18 may also include a rotation knob 24 for controlling the rotational movement of the end effector assembly 22 about a longitudinal axis "A" of the elongated shaft 12. Preferably, the ratio of rotation of the knob 24 to the end effector assembly 22 is 1:1, however, it is contemplated that gearing structure may be incorporated to increase or decrease the rotational ratio depending upon a particular purpose.

FIGS. 1B and 1C show enlarged views of the trifurcated end effector 22 which includes a first or upper multi-pronged jaw member 40 and a second or lower multi-pronged jaw member 42 which are disposed in opposing relation about pivot assembly 45. Preferably, each prong 40a, 40b, 40c and 42a, 42b, 42c of each jaw member 40 and 42, respectively, includes an electrode 41a, 41b, 41c and 43a, 43b, 43c, respectively, disposed on the inner facing surface thereof (FIG. 2). FIG. 1B shows the end effector 22 in a closed configuration and FIG. 1C shows the end effector 22 in open configuration. For the purposes herein, the term "closed" when referring to the position of the jaw members relative to one another means to bring the jaw members together in close proximity relative to one another without the electrodes actually contacting one another.

As best seen in FIG. 2, each electrode 41a, 41b, 41c and 43a, 43b, 43c is electrically coupled to a switch 71 by a cable 45a, 45b, 45c and 46a, 46b, 46c, respectively. The switch 71 is electrically coupled to an electrosurgical generator 70 by cable 73. Preferably, switch 71 selectively imparts different electrical potentials to specific electrodes 41a, 41b, 41c and 43a, 43b, 43c, respectively. Since tissue 51 is a conductor of electrical energy, when the upper and lower jaw members, 40, 42, respectively, grasp tissue 51 therebetween, the electrical energy is transferred through the tissue 51.

FIGS. 3 and 4 show alternate embodiments of an end effector assembly 122 wherein at least one of the opposing electrode pairs, e.g., 141b, 143b, is shaped to enhance a particular electrosurgical procedure or, when activated with the other electrodes, performs a dual electrosurgical purpose, e.g., cutting and sealing. More particularly and with respect to FIG. 3, electrode 141b has a V-shaped outer surface and electrode 143b has a corresponding V-shaped recess. It is contemplated that shaping the electrodes 141b, 143b in this fashion will enhance the cutting characteristics of the forceps 10. For example, during an operation a surgeon can elect to either: 1) initially seal the tissue 51 on either side of electrodes 141b, 143b by activating electrode pairs 141c, 143c and 141a, 143a and then activating the middle electrodes 141b, 143b to cut the tissue; or 2) the surgeon can activate all of the electrodes 141a,b,c and 143a,b,c simultaneously to cut and weld the tissue 51 with a single discharge of electrosurgical energy. It may be that the cutting is done by pulsing a high voltage pulse between electrodes 141b and 143b. The pulse may be at the RF frequency or alternately at DC levels.

FIG. 4 shows another embodiment of the end effector 222 wherein electrode 241b includes a notch and electrode 243b includes a corresponding recess which is dimensioned to receive the notch to enhance electrosurgical sealing.

It is contemplated that electrodes 241a,b,c and 243a,b,c may be shaped with a variety of mechanically complimentary surfaces to enhance electrosurgical sealing, coagulating, cauterizing and/or cutting. Moreover, it is also envisioned that one electrode pair, 241b, 243b, may be vertically offset from another electrode pair 241a, 243a (and/or 241c, 243c) which may also enhance a particular electrosurgical procedure. Moreover, it is also envisioned that end effector assembly 22 can have more or less prongs depending upon a particular purpose. For example, FIG. 5 depicts an end effector assembly 922 which includes two pair of opposing prongs 940a, 942a and 940b, 942b with opposing electrodes 941a, 943a and 941b, 943b, respectively disposed thereon.

In use and as best seen in FIGS. 6 and 7, the surgeon manipulates handle 26 (FIG. 1A) to advance the activator assembly 20 and move jaw members 40, 42 (FIG. 1C) to the open position wherein the jaw members 40, 42 are disposed in spaced relation relative to one another to receive tissue 51 therebetween (FIG. 6). The surgeon then manipulates handle 26 to impart movement of the jaw members 40, 42 about pivot 45 (FIG. 1B) to close the inner facing surfaces of the jaw members 40, 42 about tissue 51 (FIG. 7). By controlling the intensity, frequency and duration of the electrosurgical energy applied to the tissue 51, and, to a certain extent, by controlling the mechanical clamping pressure applied to the tissue 51, the surgeon can either seal, cauterize, coagulate/desiccate and/or cut tissue and/or simply reduce or slow bleeding. The mating electrodes may also have complimentary surfaces that are rounded, notched or triangular for the purpose of increasing their surface area and thus increasing the seal width.

It is contemplated that various electrosurgical generators can be employed to seal, cauterize, coagulate/desiccate and/or cut tissue and/or simply reduce or slow bleeding, e.g., those generators described in U.S. Pat. Nos. 4,658,819, 4,658,820, 4,827,927 and 5,514,129 the contents of which are incorporated herein by reference.

It is contemplated that switch 71 (FIG. 2) selectively controls each individual electrode and can activate the electrodes 41a, 41b, 41c, 43a, 43b, 43c simultaneously, sequentially, in pairs, and/or in various combinations. For example, FIGS. 8A–13B show several electrode activation schemes for sealing, cauterizing, coagulating and/or cutting tissue 51. In particular, FIGS. 8A and 8B show one particular electrode activation sequence wherein opposing electrodes 341b and 343b are initially activated such that electrosurgical current flows between electrodes 341b, 343b and through tissue 51 to form a seal 360b therebetween (see FIG. 8A). After seal 360b is formed, electrodes pairs 341a, 343a and 341c, 343c are activated to form seals 360a and 360c (FIG. 8B) on either side of seal 360b. As can be appreciated from the present disclosure, the surgeon can easily create multiple seals without having to physically manipulate and/or re-position the forceps 10 which is particularly advantageous when creating multiple seals.

It is contemplated that by initially sealing the tissue 51 between the center pair of electrodes 341b, 343b, the steam which disseminates along the tissue 51 as the tissue 51 boils and desiccates will be minimized which reduces the chances of accidentally opening the outer seals 360a, 360c.

FIGS. 9A–9C show another possible activation sequence wherein opposing electrode pairs 441c and 443c, 441b and 443b, 441a and 443a are activated sequentially to form seals 460c, 460b and 460a, respectively. FIG. 10 depicts another activation sequence wherein all of the electrode pairs, namely, 541c and 543c, 541b and 543b, 541a and 543a are activated simultaneously forming seals 560c, 560b and 560a, respectively.

FIGS. 11A and 11B shows yet another activation sequence wherein vertically off-set electrodes 641c and 643b are initially simultaneously activated such that electrosurgical energy travels between electrodes 641c and 643b and through tissue 51 in an angular manner creating a first cross-seal 660c. A second cross-seal is subsequently created in a similar manner by activating electrodes 641b and 643c. As best seen in FIG. 11B, forming seals 660c and 660b in this manner creates an X-like cross-seal in tissue 51.

FIG. 12 shows a similar activation sequence wherein electrodes 741c, 741a and 743b are activated simultaneously such that electrosurgical energy travels from each outer electrode 741c and 741a towards lower center electrode 743b creating two cross-seals 760a and 760b.

FIGS. 13A and 13B show still another activation sequence wherein vertically off-set electrodes 841c and 843b are initially activated to form cross-seal 860b between electrodes 841c and 843b. Electrodes 841b and 843a are subsequently activated to form cross-seal 860a between electrodes 841b and 843a.

From the foregoing and with reference to the various figure drawings, those skilled in the art will appreciate that certain modifications can also be made to the present disclosure without departing from the scope of the present disclosure. For example, it is contemplated that other activation sequences can be easily employed by selectively controlling switch 71 to form a variety of different seals and cross-seals between the electrodes. It is also contemplated that the switch can selectively control the amount of electrosurgical energy flowing to each electrode to allow a surgeon to coagulate, cauterize and/or cut vessels and vascular tissue.

Although it is preferable to vertically align the electrodes on the jaw members, in some cases it may be preferable to offset the opposing electrodes relative to one another either longitudinally or transversely to suit a particular purpose.

In addition, it may be preferable to add other features to the forceps, e.g., an articulating assembly to axially displace the end effector assembly relative to the elongated shaft.

In some cases it may be-preferable to include other mechanisms to control and/or limit the movement of the jaw members 40 and 42 relative to one another. For example, a ratchet and pawl system could be utilized to segment the movement of the two handles 26 and 28 into discrete units which will, in turn, impart discrete movement to the jaw members 40 and 42 relative to one another.

End effector 22 or forceps 10 may include a stop member which is designed to restrict and/or regulate movement of the electrodes relative to one another in order to assure that the correct force is applied to seal, cauterize, coagulate and/or cut the tissue 51.

Although the various figure drawings depict the end effector having a pair of multi-pronged opposing jaw members, in some cases it may be preferable to have only one jaw member with multiple prongs. In other cases, it may be preferable to have a different number of prongs associated with each jaw member to enhance cross-sealing between electrodes.

ALTERNATE EMBODIMENTS

Alternatively, another embodiment of the present disclosure (not shown in the drawings) may include jaw members which are not multi-pronged but, rather, include a plurality of conductive strips which extend distally from each jaw member. For example, in one embodiment, a block of non-conductive material, e.g., plastic, includes a plurality of conductive strips which can be selectively activated to achieve a desired effect similar to the prongs described above with respect to FIGS. 3–13B. Preferably, the strips are flat, recessed or offset from the block and may be formed having various cross sections, e.g., V-shaped, notched, or round which it is envisioned will effect the overall width of the seal. Moreover, one jaw member, e.g., the upper jaw member, may include at least two distally-extending conductive strips while the lower jaw member preferably includes at least one opposing conductive strip.

It is envisioned that the conductive strips can be activated simultaneously or sequentially similar to the activation sequences described above with respect to FIGS. 8A–13B. Moreover, it is contemplated that opposing conductive strips can be offset relative to one another either longitudinally or transversely to suit a particular purpose.

There have been described and illustrated herein several embodiments of a multi-pronged bipolar forceps which allows a user to selectively seal, cauterize, coagulate/ desiccate and/or cut vessels and vascular tissue at multiple sites without manipulating the forceps. While particular embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. A bipolar forceps, comprising:
    a pair of jaw members operatively mounted in opposing relation relative to one another, said jaw members being selectively movable from a first open position wherein said jaw members are disposed in spaced relation relative to one another to a second clamping position wherein said jaw members are disposed in a close juxtaposed relation;
    each of said jaw members having a plurality of distally extending prongs thereon;
    at least one electrode disposed on an inner facing surface of at least two prongs of one of said jaw members and at least one electrode disposed on an inner facing surface of at least one prong of the other of said jaw members; and
    a switch for selectively controlling electrosurgical energy to at least two electrodes disposed on one of said jaw members and one electrode disposed on the other of said jaw members.

2. A bipolar forceps according to claim 1 wherein said electrodes on said first and second jaw members are arranged in opposing pairs.

3. A bipolar forceps according to claim 1 wherein the inner facing surfaces of at least one electrode pair has a complimentary cross-section.

4. A bipolar forceps according to claim 3 wherein the inner facing surfaces of at least one electrode pair has a V-shaped cross-section.

5. A bipolar forceps according to claim 3 wherein the inner facing surfaces of at least one electrode pair has a notched cross-section.

6. A bipolar forceps according to claim 3 wherein the inner facing surfaces of at least one electrode pair has a rounded cross-section.

7. A bipolar forceps according to claim 1 wherein said first and second jaw members are bifurcated.

8. A bipolar forceps according to claim 1 wherein said first and second jaw members are trifurcated.

9. A method of applying electrosurgical energy to tissue, comprising the steps of:
    a) providing a bipolar forceps having:
        a pair of jaw members operatively mounted in opposing relation relative to one another, said jaw members being selectively movable from a first open position wherein said jaw members are disposed in spaced relation relative to one another to a second clamping position wherein said jaw members are disposed in a close juxtaposed relation;
        each of said jaw members having a plurality of distally extending prongs thereon;
        at least one electrode disposed on an inner facing surface of at least two prongs of one of said jaw members and at least one electrode disposed on an inner facing surface of at least one prong of the other of said jaw members; and
        a switch for selectively controlling electrosurgical energy to at least two electrodes disposed on one of said jaw members and one electrode disposed on the other of said jaw members;
    b) grasping tissue between said jaw members;
    c) selectively activating a first electrode on one of said prongs of said first jaw member; and
    d) selectively activating a second electrode on one of said prongs of said second jaw member such that electrosurgical energy is transferred from the first jaw member, through the tissue and to the second jaw member.

10. A method according to claim 9 further comprising the steps of:

a) selectively activating additional electrodes on additional prongs of said first and second jaw members to treat tissue at multiple sites without manipulation of the forceps.

11. A method according to claim 10 wherein said first and second electrodes and said additional electrodes of said activating steps are multiplexed.

12. A method according to claim 9 wherein said electrodes of said providing step are generally aligned on said inner facing surfaces of said jaw members in opposing pairs.

13. A method according to claim 10 wherein said first and second electrodes and said additional electrodes of said activating steps are activated sequentially.

14. A method according to claim 10 wherein said first and second electrodes and said additional electrodes of said activating steps are activated simultaneously.

15. A method according to claim 9 wherein said first and second electrodes of said activating steps are off-set relative to one another.

16. A method of sealing vessels, comprising the steps of:

a) providing a bipolar forceps having:

a pair of jaw members operatively mounted in opposing relation relative to one another, each of said jaw members being selectively movable from a first open position wherein said jaw members are disposed in spaced relation relative to one another to a second clamping position wherein said jaw members are disposed in a close juxtaposed relation;

each of said jaw members having a plurality of distally extending prongs thereon;

at least one pair of opposing electrodes disposed on each opposing pair of prongs of said jaw members, and a switch for selectively controlling electrosurgical energy to each electrode pair;

b) grasping tissue between said jaw members; and c) selectively activating said electrodes pairs to form a seal between each pair of opposing electrodes without manipulation of the forceps.

17. A method according to claim 16 wherein said jaw members of said providing step are bifurcated.

18. A method according to claim 16 wherein said jaw members of said providing step are trifurcated.

* * * * *